US011105749B2

(12) United States Patent
Nogami et al.

(10) Patent No.: US 11,105,749 B2
(45) Date of Patent: Aug. 31, 2021

(54) INFORMATION PROCESSING APPARATUS, INFORMATION PROCESSING METHOD AND PROGRAM

(71) Applicant: CANON KABUSHIKI KAISHA, Tokyo (JP)

(72) Inventors: Atsushi Nogami, Kawasaki (JP); Mamoru Yoshimoto, Yokohama (JP); Nobuaki Kuwabara, Yokohama (JP); Yusuke Mitarai, Tokyo (JP); Yasuhiro Komori, Tokyo (JP); Masakazu Matsugu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 34 days.

(21) Appl. No.: 16/240,352

(22) Filed: Jan. 4, 2019

(65) Prior Publication Data
US 2019/0137409 A1 May 9, 2019

Related U.S. Application Data

(63) Continuation of application No. PCT/JP2017/022444, filed on Jun. 19, 2017.

(30) Foreign Application Priority Data

Jul. 6, 2016 (JP) .............................. JP2016-134421

(51) Int. Cl.
*G01N 21/88* (2006.01)
*G06T 1/00* (2006.01)
(Continued)

(52) U.S. Cl.
CPC ......... *G01N 21/8851* (2013.01); *G01N 21/84* (2013.01); *G01N 29/0609* (2013.01);
(Continued)

(58) Field of Classification Search
CPC combination set(s) only.
See application file for complete search history.

(56) References Cited

U.S. PATENT DOCUMENTS 4,460,273 A * 7/1984 Koizumi ................ G01N 21/89
250/559.49
6,427,024 B1 * 7/2002 Bishop ................. G01R 31/311
348/126
(Continued)

FOREIGN PATENT DOCUMENTS

CN 103364408 A 10/2013
CN 104718428 A 6/2015
(Continued)

OTHER PUBLICATIONS

Grasset, R., et al., "Image-Driven View Management for Augmented Reality Browsers", IEEE, Nov. 2012, pp. 177-186.
(Continued)

*Primary Examiner* — Zhiyu Lu
(74) *Attorney, Agent, or Firm* — Canon U.S.A., Inc., IP Division

(57) ABSTRACT

It is an object of the present invention to provide a user interface which facilitates confirmation of an area in an image and associated data corresponding to the area without requiring user's complicated operations. To achieve the object, an information processing apparatus comprises: an obtaining unit configured to obtain a first image including a plurality of objects, and information related to respective positions of the plurality of objects in the first image; and a determining unit configured to determine a position in case of shifting and displaying a second image indicating the plurality of objects with respect to the first image, based on the obtained positions of the plurality of objects.

19 Claims, 16 Drawing Sheets

(51) Int. Cl.
*G01N 21/84* (2006.01)
*G01N 29/06* (2006.01)
*G01N 33/38* (2006.01)
*G06F 3/0481* (2013.01)
*G06T 7/00* (2017.01)

(52) U.S. Cl.
CPC ......... *G01N 33/383* (2013.01); *G06F 3/0481* (2013.01); *G06T 1/00* (2013.01); *G06T 1/0007* (2013.01); *G06T 7/0004* (2013.01)

(56) References Cited

U.S. PATENT DOCUMENTS

| | | | |
|---|---|---|---|
| 8,134,554 B1 | 3/2012 | Huang et al. | |
| 2012/0056881 A1* | 3/2012 | Yamaji | H04N 13/128 345/419 |
| 2012/0140212 A1* | 6/2012 | Suga | G01N 21/9501 356/237.3 |
| 2012/0141011 A1* | 6/2012 | Sakai | G06T 7/001 382/149 |
| 2013/0143150 A1* | 6/2013 | Choi | G03F 1/44 430/5 |
| 2014/0307946 A1* | 10/2014 | Nakahira | G06T 7/0004 382/149 |
| 2015/0213596 A1* | 7/2015 | Tandi | G01N 21/9501 382/149 |
| 2015/0228063 A1* | 8/2015 | Minakawa | G06K 9/52 382/151 |
| 2016/0004927 A1 | 1/2016 | Yonaha | |
| 2018/0156736 A1* | 6/2018 | Kondo | G06T 7/0008 |

FOREIGN PATENT DOCUMENTS

| | | |
|---|---|---|
| CN | 104903712 A | 9/2015 |
| CN | 105606030 A | 5/2016 |
| JP | H05-242178 A | 9/1993 |
| JP | H10-105678 A | 4/1998 |
| JP | 2002-257744 A | 9/2002 |
| JP | 2007-180904 A | 7/2007 |
| JP | 2009-28515 A | 2/2009 |
| JP | 2014-228357 A | 12/2014 |
| JP | 2015-32069 A | 2/2015 |
| WO | 2014/156429 A1 | 10/2014 |
| WO | 2016/039041 A1 | 3/2016 |

OTHER PUBLICATIONS

Azuma, R., et al., "Evaluating Label Placement for Augmented Reality View Management", IEEE, 2003.

Zhang, W., et al., "Automatic Crack Detection and Classification Method for Subway Tunnel Safety Monitoring", Sensors, 2014, pp. 19307-19328, vol. 14.

* cited by examiner

FIG. 4

| ID | KIND OF DEFECT | COORDINATES | NOTE |
|---|---|---|---|
| C001 | CRACK | $x_{C001\_1}, y_{C001\_1}, \cdots x_{C001\_n}, y_{C001\_n}$ | 0.2mm |
| C002 | CRACK | $x_{C002\_1}, y_{C002\_1}, \cdots x_{C002\_m}, y_{C002\_m}$ | 0.5mm |
| E001 | DEPOSIT | $x_{E001\_1}, y_{E001\_1}, \cdots x_{E001\_q}, y_{E001\_q}$ | |
| ... | ... | ... | |
| Cxxx | CRACK | $x_{Cxxx\_1}, y_{Cxxx\_1}, \cdots x_{Cxxx\_p}, y_{Cxxx\_p}$ | 0.5mm |

FIG. 10

|  | r | θ |
|---|---|---|
| $p_1$ | 5 PIXELS | 0° |
| $p_2$ | 5 PIXELS | 45° |
| $p_3$ | 5 PIXELS | 90° |
| . | . | . |
| . | . | . |
| $p_m$ | 10 PIXELS | 315° |

INFORMATION PROCESSING APPARATUS, INFORMATION PROCESSING METHOD AND PROGRAM

CROSS-REFERENCE TO RELATED APPLICATIONS

This application is a continuation of International Application No. PCT/JP2017/022444, filed Jun. 19, 2017, which claims the benefit of Japanese Patent Application No. 2016-134421, filed Jul. 6, 2016, both of which are hereby incorporated by reference herein their entirety.

BACKGROUND OF THE INVENTION

Field of the Invention

The present invention relates to an information processing apparatus, an information processing method, and a storage medium.

Description of the Related Art

Conventionally, in inspection of concrete wall surfaces of bridges, dams, tunnels and the like, investigation engineers approach the concrete wall surface and record defects such as cracks and the like by visual inspection. Working costs of such an inspecting operation called close visual inspection are high. For this reason, a method of automatically detecting a defect from an image obtained by capturing a concrete surface has been proposed. Japanese Patent Application Laid-Open No. 2014-228357 discloses a technique of automatically detecting a crack from a concrete wall surface image by using a wavelet transform.

Besides, since accuracy of such automatic detection is not sufficient, erroneous detection and non-detection occur. For this reason, it is necessary for the investigation engineer and/or an investigation responsible person to confirm and appropriately correct defect data indicating a result of the automatic detection and the concrete wall surface image. In the relevant confirmation and correction, in order to simultaneously browse the concrete wall surface image and the defect data, the defect data is generally superposed and displayed on the concrete wall surface image.

Japanese Patent Application Laid-Open No. H10-105678 discloses a technique of, based on a movement instructing operation by a user, moving, deforming and displaying a contour line of an organ extracted from a medical image in order to decide whether or not the contour line is correct.

However, when the defect data is superposed and displayed on the image, it becomes difficult to browse the image of the portion corresponding to the defect data, so that there is a case where it is difficult to decide whether or not the defect data is correct. It is possible to facilitate the browsing by moving and deforming the defect data by using the method disclosed in Japanese Patent Application Laid-Open No. H10-105678. However, in the method of Japanese Patent Application Laid-Open No. H10-105678, it is necessary for a user to manually adjust parameters of the movement and deformation of the contour line. For this reason, it is necessary for the user to each time adjust appropriate parameters facilitating the browsing with respect to an image being displayed, which makes a browsing operation of the user complicated.

SUMMARY OF THE INVENTION

The present invention has been completed in view of such problems as described above, and aims to provide a user interface which facilitates a confirming operation for defect data (object) in an image and an image showing the object without requiring user's complicated operations.

Therefore, the present invention provides an information processing apparatus which is characterized by comprising: an obtaining unit configured to obtain a first image including a plurality of objects, and information related to respective positions of the plurality of objects in the first image; and a determining unit configured to determine a position in case of shifting and displaying a second image indicating the plurality of objects with respect to the first image, based on the obtained positions of the plurality of objects.

Further features of the present invention will become apparent from the following description of exemplary embodiments with reference to the attached drawings.

BRIEF DESCRIPTION OF THE DRAWINGS

FIG. 4 is a diagram for explaining defect data.

FIG. 10 is a diagram for explaining another example of a method of determining the offset parameter.

DESCRIPTION OF THE EMBODIMENTS

Hereinafter, preferred embodiments of the present invention will be described in detail with reference to the attached drawings.

First Embodiment

An information processing apparatus according to the first embodiment stores and displays a captured image of a wall surface, for example, in order to support inspection and management of wall surfaces and the like of concrete structures such as a bridge, a dam, a tunnel and the like. Moreover, the information processing apparatus displays a defect area which is a confirmation object for which visual confirmation by an administrator is necessary in the inspection and management.

Incidentally, the object to be managed is not limited to the wall surface of the concrete structure. Namely, road asphalt is used another example of the object of inspection and management. Besides, the defect area to be managed is an area in which a defect, i.e., a state change, is occurring. As the defects, there are a crack, deposit of free lime, honeycomb, cold joint, exposure of steel bar, and the like in the concrete structure. However, the defects are not limited to those described in the embodiment. Besides, the captured image is assumed to be a visible light image (RGB image), but the kind of image is not limited thereto. As another example, the captured image may be a thermal image captured by an infrared camera, an image captured by a line sensor camera, or the like. Incidentally, the captured image of the wall surface of the concrete structure is an example of the image.

FIGS. 1A to 1D are diagrams showing display examples of a window of a GUI application of the information processing apparatus. An outline of the information processing apparatus according to the present embodiment will be described with reference to FIGS. 1A to 1D. In a window 100 shown in FIG. 1A, a captured image 101 of a concrete wall surface is displayed, and the captured image 101 includes a cracked defect area 102.

Figure 1A:
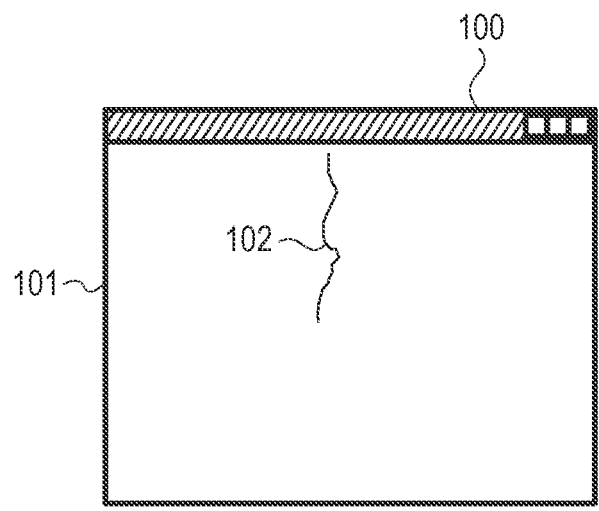
FIG. 1A is a diagram showing a display example of a window of a GUI application of an information processing apparatus.
Figure 1B:
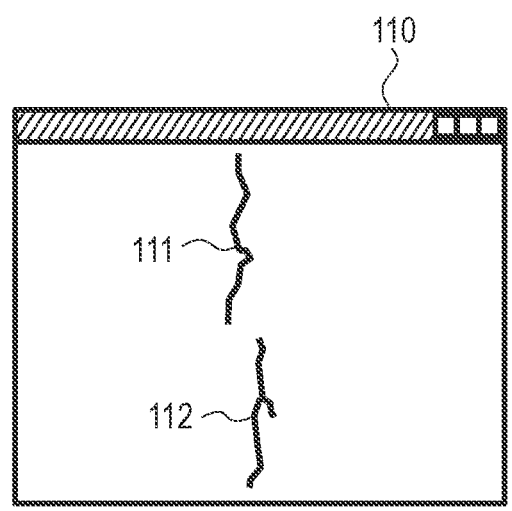
FIG. 1B is a diagram showing a display example of the window of the GUI application of the information processing apparatus.
Figure 1C:
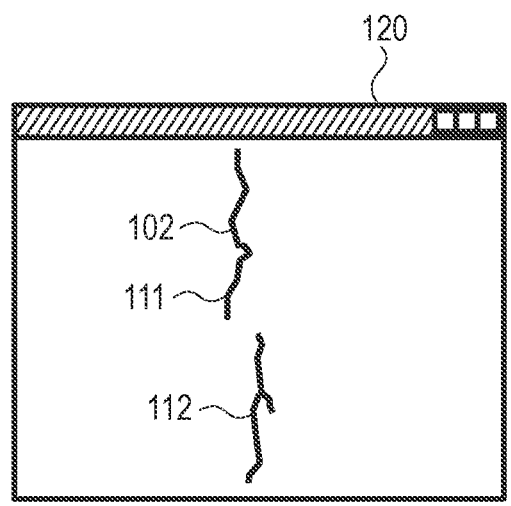
FIG. 1C is a diagram showing a display example of the window of the GUI application of the information processing apparatus.

Further, in a window 110 shown in FIG. 1B, defect data 111 and 112 obtained by an automatic detecting process from the captured image 101 of FIG. 1A are visualized and displayed. Here, it is assumed that there is actually no change in the area of the captured image 101 corresponding to the defect data 111, and the defect data 111 is an erroneous detection result. Incidentally, in the drawings of the present embodiment, a thin line indicates an actual crack which can be observed on the concrete wall surface image, and a thick line indicates deformation data displayed in an application window. For the sake of convenience of display on paper, the defect data is represented by thick lines, but on the actual application window, it is preferable to display the defect data by using a displaying method such as displaying it with color.

A user such as a defect administrator, a data input person or the like visually observes defect data and confirms whether or not the defect data corresponds to a defect of a captured image. At this time, in order for the user to simultaneously browse the defect of the captured image and the visualized defect data, it is preferable to visualize the defect data and superpose and display the visualized defect data on the captured image. In a window 120 shown in FIG. 1C, an image obtained by superposing, on the captured image (first image) 101 of FIG. 1A, an image (second image) in which the defect data 111 and 112 are visualized and indicate the position of the defect is displayed (first display mode). Here, since the defect area 102 corresponding to the actual crack in the captured image and the defect data 111 substantially overlap each other, it is difficult for the user to confirm the cracked area in the captured image. Likewise, it is difficult to browse the area of the captured image corresponding to the defect data 112 based on the erroneous detection result.

Figure 1D:
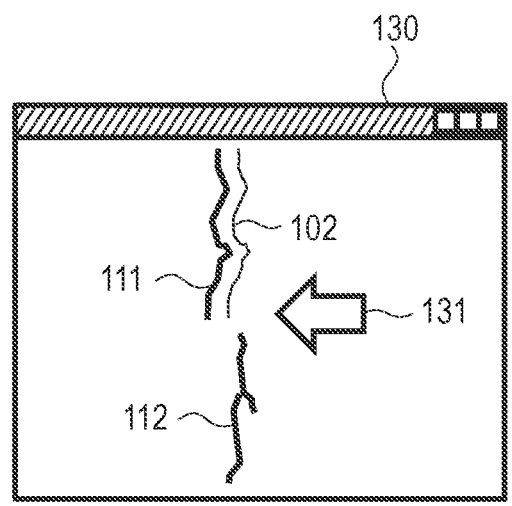
FIG. 1D is a diagram showing a display example of the window of the GUI application of the information processing apparatus.

In a window 130 shown in FIG. 1D, an image obtained by moving the display positions of the defect data 111 and 112 in the direction of an arrow 131 and then superposing these data on the captured image 101 is displayed (second display mode). By displaying the data as shown in FIG. 1D, it is easy to browse the defect area 102 and the image portion of the defect data 112. Like this, offset display, in which the defect data is moved and displayed in a superposing manner, is an effective displaying method. However, when moving and displaying the defect data as in FIG. 1D, it is necessary to move the defect data by setting appropriate movement direction and movement amount (an arrow 131 in FIG. 1D) according to the captured image and the defect data. On the other hand, the information processing apparatus according to the present embodiment automatically or semi-automatically determines an appropriate display position of defect data and displays a captured image with the defect data superposed on the display position.

Figure 2:
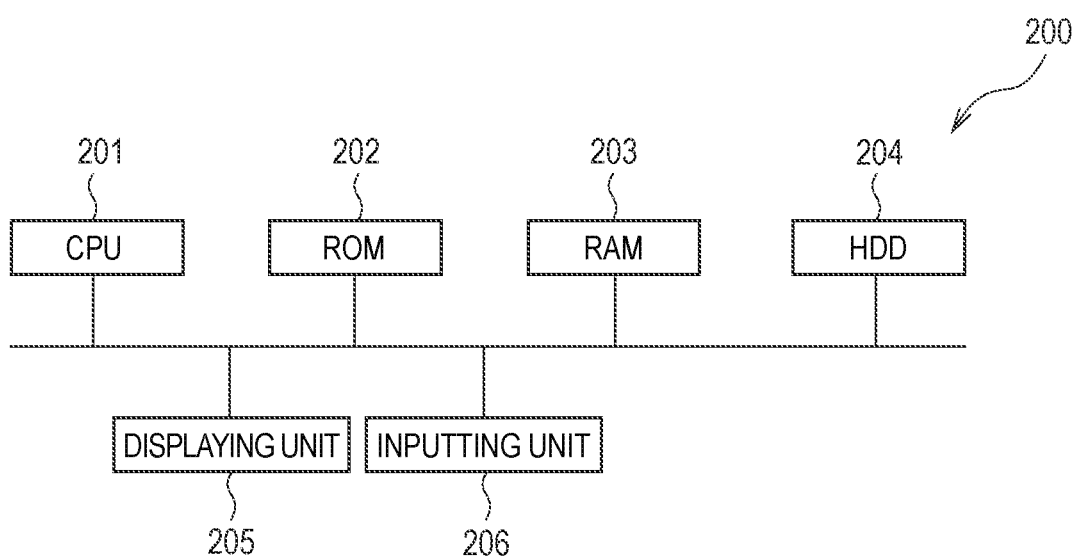
FIG. 2 is a diagram showing a hardware constitution of the information processing apparatus.

FIG. 2 is a diagram showing a hardware constitution of an information processing apparatus 200 according to the first embodiment. The information processing apparatus 200 comprises a CPU 201, a ROM 202, a RAM 203, an HDD 204, a displaying unit 205, an inputting unit 206, and a communicating unit. The CPU 201 reads a control program stored in the ROM 202 and performs various processes based on the read program. The RAM 203 is used as temporary storage areas such as a main memory, a working area and the like of the CPU 201. The HDD 204 stores various data, various programs and the like. Later-described functions and processes of the information processing apparatus 200 are realized when the CPU 201 reads the programs stored in the ROM 202 or the HDD 204 and executes the read programs. The displaying unit 205 displays various kinds of information. The inputting unit 206 comprises a keyboard and a mouse, and accepts various user's operations. As other examples, the inputting unit 206 may be a pen tablet, and the displaying unit 205 and the inputting unit 206 may be combined as a tablet.

Figure 3:
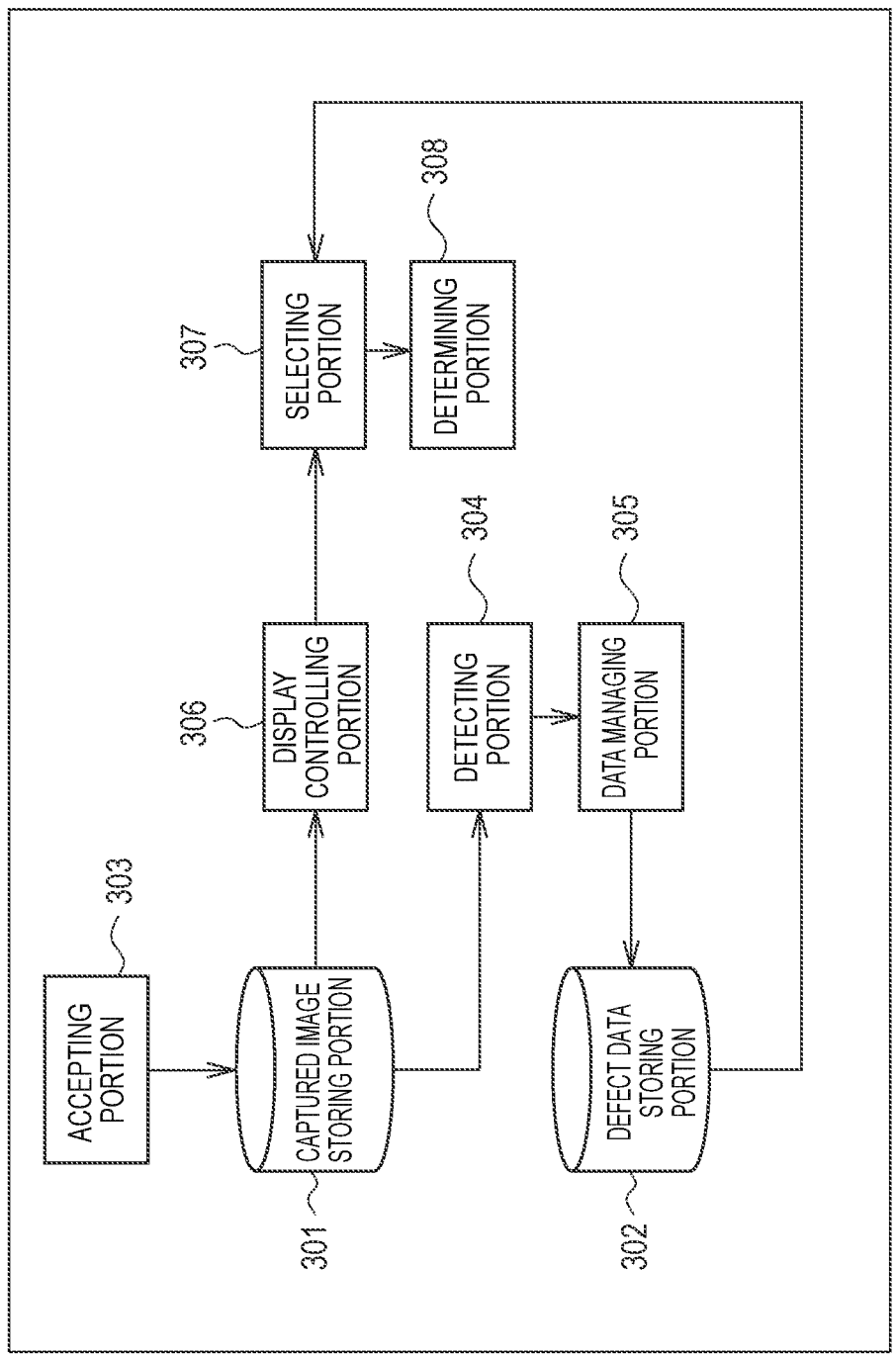
FIG. 3 is a diagram showing a software configuration of the information processing apparatus.

FIG. 3 is a diagram showing a software configuration of the information processing apparatus 200. The information processing apparatus 200 includes a captured image storing portion 301, a defect data storing portion 302, an accepting portion 303, a detecting portion 304, a data managing portion 305, a display controlling portion 306, a selecting portion 307, a determining portion 308. The captured image storing portion 301 stores captured images. In the present embodiment, it is assumed that the captured image is a face-to-face image which directly faces a concrete wall surface, that is, an image which is captured in the direction perpendicular to the concrete wall surface as the capturing direction. Depending on position and orientation of a structure at the time of capturing, it is often impossible to capture an image facing the concrete wall surface. In this case, the information processing apparatus 200 creates a face-to-face image by a geometric transforming process of an image and stores it in the captured image storing portion 301 as a captured image.

The defect data storing portion 302 stores defect data. As shown in FIG. 4, the defect data storing portion 302 stores an ID, a kind of defect and a display position in association with others. Here, the ID is identification information of the defect data. The kind of defect is information indicating the kind of defect including a crack, a deposit and the like. The coordinates are information for identifying the position on the captured image in which the defect is detected, specifically, coordinate values in the coordinate system of the captured image.

For a cracked defect, the values of the two-dimensional coordinates of n points from $(x_{C001\_1}, y_{C001\_1})$ to $(x_{C001\_n}, y_{C001\_n})$ are recorded. Incidentally, the coordinate values are not limited to the coordinates in the coordinate system of the captured image, but may be values in the coordinate system of the real space in which the structure exists. Moreover, as a remark, information of a thickness of a crack is also stored as the cracked defect data included in the kind of defect.

ID=E001 corresponds to the defect of the deposit. Unlike the crack, the deposit is a defect having an area. Therefore, the coordinates from $(x_{E001\_1}, y_{E001\_1})$ to $(x_{E001\_1}, y_{E001\_q})$ are recorded as the display position, and the range of the defect data is the range (range of E001 of FIG. 5) surrounded by these coordinates.

Figure 5:
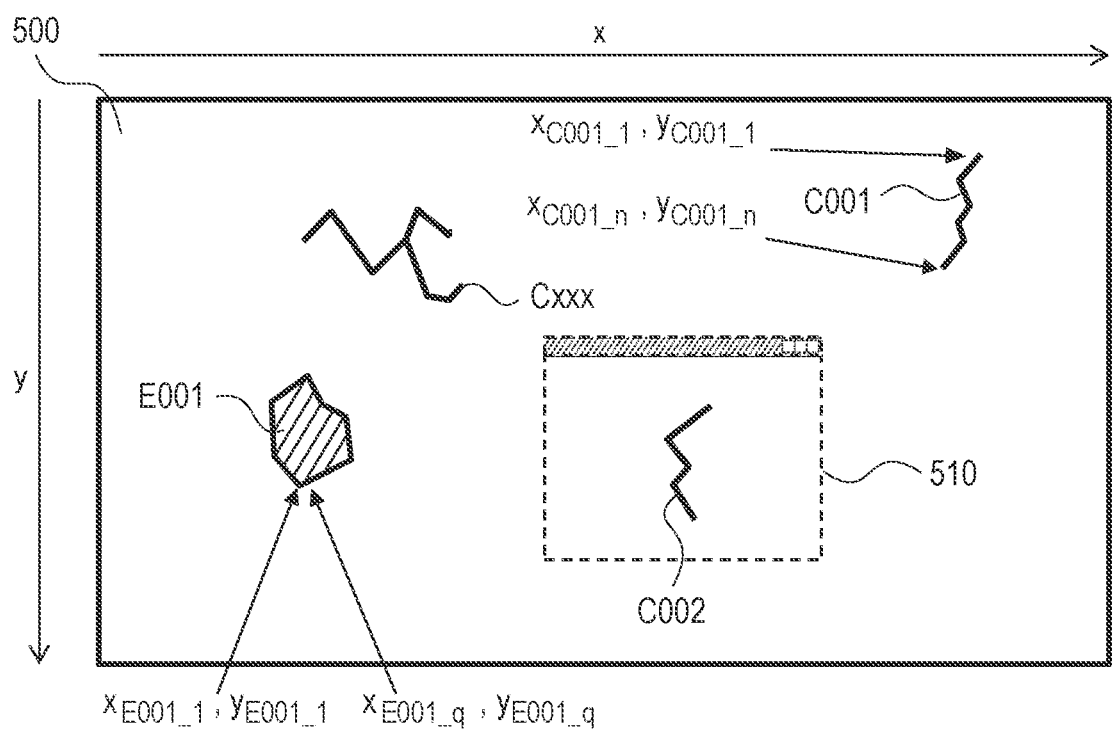
FIG. 5 is a diagram for explaining a relationship between a captured image and the defect data.

Next, with reference to FIG. 5, a relationship between the captured image and the defect data will be described. The captured image is a high-resolution image in order to observe a minute defect such as the crack or the like. Therefore, the entire captured image of a certain structure is generally an image having a very large data size. A captured image 500 shown in FIG. 5 is a large image (for example, an image of 100,000×100,000 pixels or more) of the wall surface of a structure, and has an image coordinate system of x axis and y axis. Even if browsing the whole of such the large captured image 500, it is difficult to confirm the fine defect on the concrete wall surface. Therefore, in general, a part of the captured image 500 is enlarged and browsed.

For example, a window 510 in FIG. 5 is application software which displays only a part of the captured image 500. In the window 510, the part of the captured image 500 is enlarged and displayed, and in correspondence therewith, defect data C002 superposed on the defect area is also enlarged and displayed. Therefore, the user can confirm the detailed state. Normally, at the time of confirming the defect, the user enlarges and browses an arbitrary portion of the concrete wall surface image in this way. The information processing apparatus 200 enlarges and displays a partial area of the captured image in the window during the confirming operation by the user.

A crack C001 shown in FIG. 5 is represented by a polyline determined by the coordinate values of n points (six points in the drawing) from $(x_{C001\_1}, y_{C001\_1})$ to $(x_{C001\_n}, y_{C001\_n})$ or the like. As just described, in the present embodiment, it is assumed that the cracked defect data is represented by the polyline. Incidentally, the cracked defect data may be represented by a line of thickness corresponding to a crack thickness, or may be represented by a color line corresponding to the crack thickness. The defect data is not limited to be represented by the polyline, but may be represented by a curve. When the defect data is represented by the curve, a detailed image expression is possible, but a data capacity increases.

Returning to FIG. 3, the accepting portion 303 accepts an input of a captured image and stores the captured image in the captured image storing portion 301. Incidentally, the captured image may be input from an external device via a network or the like, and, as another example, the information processing apparatus 200 may comprise a capturing unit (not illustrated) and the captured image may be input from the capturing unit.

The detecting portion 304 automatically detects a defect area from the captured image. An automatic detecting method of the defect area is not particularly limited, but it is possible to use the conventional technique described in Japanese Patent Application Laid-Open No. 2014-228357, for example. Further, as another example of the automatic detecting method, it is also possible to use a method of previously learning a feature of defect from a defective image and detecting the defect based on such a learning result. As an automatic detecting method of the defects based on the learning, for example, the following document can be referred.

Zhang, Wenyu, et al. "Automatic crack detection and classification method for subway tunnel safety monitoring" Sensors 14.10 (2014): 19307-19328

Based on the detection result by the detecting portion 304, the data managing portion 305 records the information related to the defect area as the defect data in the defect data storing portion 302. More specifically, the data managing portion 305 assigns a new ID to the defect data, and records the new ID in the defect data storing portion 302. Further, the data managing portion 305 identifies the kind of defect based on the detected shape of the defect, and records the identified defect data in the defect data storing portion 302 in association with the new ID. The data managing portion 305 also identifies the position of the defect area in the captured image, and records the identified position in the defect data storing portion 302 in association with the new ID.

As another example, the defect area may be identified according to a user's operation input. In this case, the information processing apparatus 200 records the defect data according to the user operation. More specifically, the displaying unit 205 displays the captured image. Then, the user visually confirms the position of the defect such as the crack or the like, and designates the defect area by designating the position on the captured image via the inputting unit 206. Then, the data managing portion 305 records the information related to the defect area designated by the user as the defect data in the defect data storing portion 302. Incidentally, the defect data storing portion 302 only has to store the defect data, and a method of generating the defect data is not limited to that described the embodiment. The defect data storing portion 302 may store the plurality of defect data respectively obtained by different methods such as automatic detection, a user input and the like.

The user performs an operation of confirming whether or not these defect data are correct. For example, it is necessary for the user to confirm whether or not the input result is correct after inputting the defect data, or to confirm whether or not the automatic detection result is correct after an automatic detecting process of the defect. Besides, there is case where it is desired to confirm the defect data input by the user himself/herself even during the input operation of the defect data. In this case, based on the already input defect data, a process to be described later may be performed to create a display image and present it to the user. In this case, when the user instructs a display change, the information processing apparatus 200 calculates display parameters based on the already input defect data and performs display for browsing the captured image and the defect data.

The display controlling portion 306 controls image display on the displaying unit 205. The selecting portion 307 selects at least one piece of defect data from the plurality of defect data superposed and displayed on the captured image. The defect data selected by the selecting portion 307 is defect data to be referred to in a process of calculating display parameters of the defect data. Hereinafter, the defect data selected by the selecting portion 307 is referred to as object defect data. Here, the object defect data is an example of object data and object related data. Besides, defect data which is being displayed on the captured image and is defect data other than the object defect data (i.e., related data other than the object data) is referred to as other defect data (other related data). Incidentally, the object defect data is an example of object data to be processed. The determining portion 308 calculates the display parameter based on the object defect data.

Figure 6:
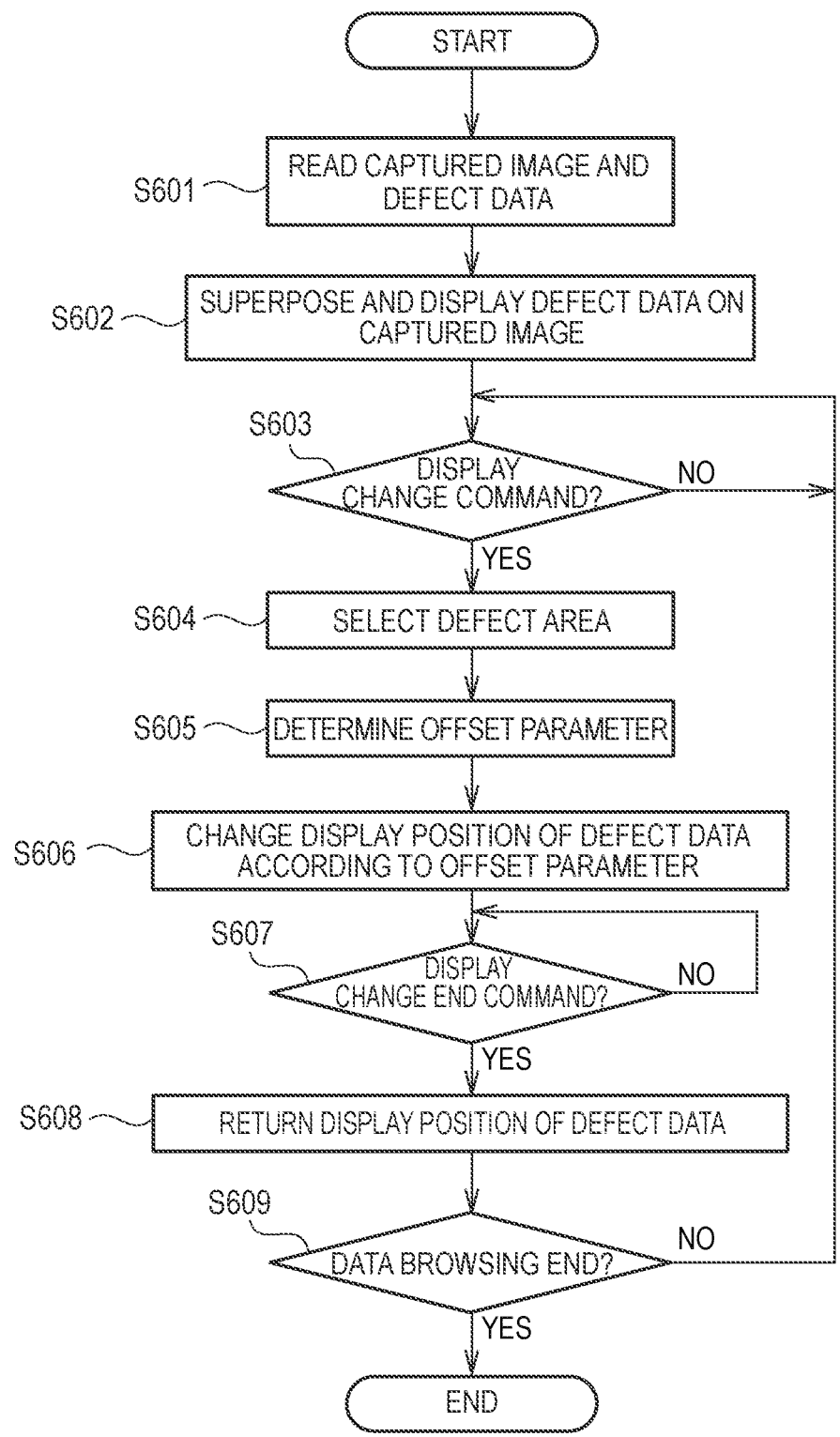
FIG. 6 is a flowchart showing a displaying process.

FIG. 6 is a flowchart showing a displaying process by the information processing apparatus 200. Incidentally, as a premise of this process, it is assumed that the captured image is stored in the captured image storing portion 301, and the defect data corresponding to the captured image is stored in the defect data storing portion 302. In S601, the display controlling portion 306 reads the captured image from the captured image storing portion 301. The display controlling portion 306 also reads the defect data from the defect data storing portion 302. Next, in S602, the display controlling portion 306 superposes and displays the corresponding defect data on the defect area of the captured image based on the defect data. More specifically, the display controlling portion 306 superposes the defect data on the position of the coordinates of the defect data. At this time, the defect data displayed on the displaying unit 205 is superposed on the defect area, for example, as shown in FIG. 1B. For this reason, the defect area of the captured image is in a state of being difficult to see.

Next, in S603, the CPU 201 confirms whether or not a display change command is accepted in response to a user operation on the inputting unit 206. This process is an example of an accepting process of the change command. When the display change command is accepted (Yes in S603), the CPU 201 advances the process to S604. When the display change command is not accepted (No in S603), the CPU 201 continues the display state. In S604, the selecting portion 307 selects the object defect data from among the plurality of defect data based on a browsing state of the user or a user instruction. In S605, the determining portion 308 determines an offset parameter. Here, the offset parameter is an example of a display parameter, and is a value indicating a movement direction and a movement amount when the display position of the defect data is moved.

Next, in S606, the display controlling portion 306 controls to move the defect data to the display position of the captured image, which is determined by the offset parameter, and to superpose and display the moved defect data. When the plurality of defect data are displayed, the display controlling portion 306 controls to move, superpose and display each of the plurality of defect data. This process is an example of a display controlling process. Next, in S607, the CPU 201 confirms whether or not a display change end command is accepted in response to a user operation on the inputting unit 206. When the display change end command is accepted (Yes in S607), the CPU 201 advances the process to S608. When the display change end command is not accepted (No in S607), the CPU 201 continues the display state.

In S608, the display controlling portion 306 returns the display position of the defect data to the display position before the movement. Next, in S609, the CPU 201 confirms whether or not a display end command is accepted in response to a user operation on the inputting unit 206. When the display end command is accepted (Yes in S609), the CPU 201 ends the displaying process. When the display end command is not accepted (No in S609), the CPU 201 advances the process to S603.

Hereinafter, details of the displaying process will be described. The display change command accepted in S603 and the display change end command accepted in S607 may be a user operation of pressing a predetermined key and a user operation of releasing a predetermined key in a pressed state, respectively. As another example, the CPU 201 may accept the display change command when the user presses a key once, and may accept the display change end command when the user presses the key again.

The user operation for inputting each command is not limited to that described in the embodiment. As another example, the CPU 201 may accept the display change command when clicking an icon on a predetermined GUI with a mouse or the like instead of the key. Besides, the user may designate the defect data desired to be browsed in detail by clicking or mouseover. In this case, the CPU 201 accepts the display change command including designation of the defect data, and in S604, the selecting portion 307 selects the defect data related to the designation as the object defect data.

Next, such a defect data selecting process in S604 will be described. For example, as shown in FIG. 5, the plurality of defect data are superposed on the captured image. If offset parameters are set in consideration of all of these defect data, display which is suitable for the defect data to which the user pays attention is not necessarily obtained. Therefore, in S604, from the plurality of defect data, the defect data to be used when determining the offset parameter is selected as the object defect data.

The selecting portion 307, for example, selects the object defect data based on a user's browsing state at the time of when the display change command is input. As described with reference to FIG. 5, in the captured image 500, the user is browsing the defect data C002. In this case, the selecting portion 307 selects the defect data C002 as the object defect data. That is, the selecting portion 307 selects the defect data being displayed, as the object defect data. Like this, by selecting the object defect data according to the user's browsing state, it is possible to determine the offset parameter according to the object defect data.

Figure 7A:
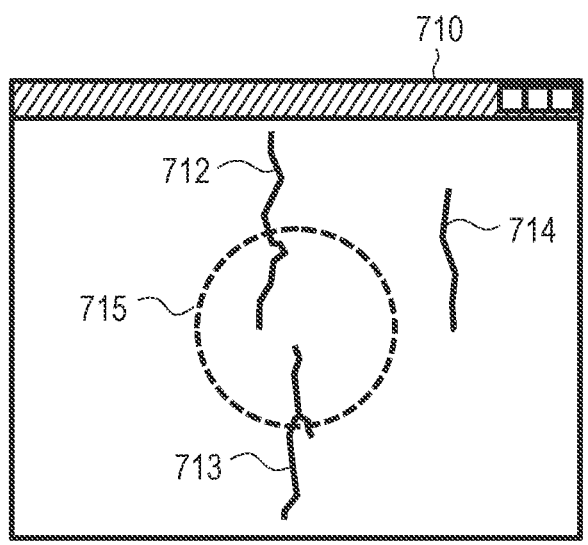
FIG. 7A is a diagram for explaining another example of a method of selecting object defect data.
Figure 7B:
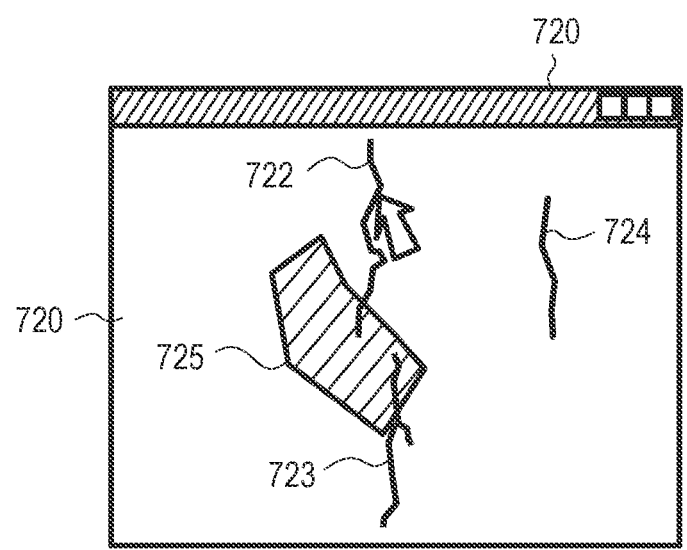
FIG. 7B is a diagram for explaining another example of the method of selecting the object defect data.

The method of selecting the object defect data is not limited to the above, and another method may be used. FIGS. 7A and 7B are diagrams for explaining other examples of the method of selecting the object defect data. In each of a window 710 of FIG. 7A and a window 720 of FIG. 7B, a captured image of a concrete wall surface is displayed. In the captured image displayed in the window 710 of FIG. 7A, cracks 712, 713 and 714 exist. With respect to this image, the selecting portion 307 may select the object defect data based on the relationship between the captured image being displayed and the display position of each defect data. For example, the selecting portion 307 selects the object defect data according to the distance between the center of the window 710 and the display position. In the example of FIG. 7A, the cracked defect data 712 and 713 of which the display positions overlap a central area 715 are selected as the object defect data, whereas the defect data 714 is not selected.

It is considered that the user tends to dispose the defect data and defect area that the user particularly pay attention to on the center of the window and browse them. Therefore, it is assumed to select the defect data existing in the vicinity of the center of the captured image being displayed like this. Thus, it is possible to select the defect data that the user particularly pays attention to as the object defect data.

As another example, the information processing apparatus 200 may further include a camera (not illustrated), and the selecting portion 307 may obtain a user's gaze direction from the captured image and select the defect data displayed ahead of the gaze direction as the object defect data.

As another example, the selecting portion 307 may select the object defect data in response to a user operation. In a case where the user selects the defect data by using a mouse cursor, the selecting portion 307 selects the selected defect data as the object defect data. Moreover, as described above, in the case where the user selects (clicks) the defect data or performs mouseover on the defect data, the information processing apparatus 200 may accept the display change command and further select the selected defect data to the object defect data.

Besides, the number of object data is not limited to one. For example, the selecting portion 307 may select all the plurality of defect data displayed on the displaying unit 205 as the object defect data. In a case where the user selects the plurality of defect data by range designation, all the selected defect data may be selected as the object defect data.

As another example, the selecting portion 307 may further select another defect data related to the selected defect data as the object defect data, in response to a user's defect data selection. For example, the selecting portion 307 selects the defect data overlapping the selected defect data and the adjacent defect data as the object defect data. In the captured image displayed in the window 720 of FIG. 7B, cracks 722, 723 and 724, and a deposit 725 exist. Here, it is assumed that the user selects the crack 722. In this case, in addition to the crack 722, the selecting portion 307 selects the defect data of the deposit 725 overlapping the crack 722 as the object defect data. Besides, when the user selects the deposit defect data 725, the selecting portion 307 selects not only the defect data 725 but also the cracked defect data 722 and 723 overlapping the defect data 725, as the object defect data.

As another example, the selecting portion 307 may further select another defect data as the object defect data in consideration of continuity with the defect data selected by the user. For example, in the example of FIG. 7B, since the respective end points of the cracked defect data 722 and 723 are close to each other and the respective directions thereof are similar to each other, there is a possibility that they are actually the continuous cracks. In such a case where the adjacent cracks exist, when the user selects the cracked defect data 722, the selecting portion 307 selects not only the cracked defect data 722 but also the defect data 723 as the object defect data.

Next, the offset parameter determining process in S605 will be described. An offset parameter p is a parameter that the defect data moves within the plane of a captured image, and is defined as Equation 1.

$$p = \begin{pmatrix} r \\ \theta \end{pmatrix} \qquad \text{Equation 1}$$

Figure 8:
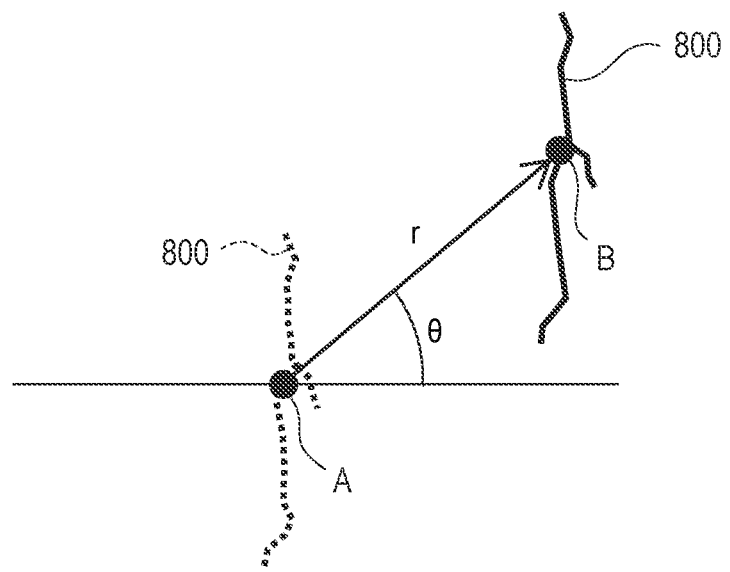
FIG. 8 is a diagram for explaining an offset parameter.

FIG. 8 is a diagram for explaining the offset parameter p. If it is assumed that a display position of defect data 800 indicated by the dotted line in FIG. 8 is A and a position of the movement destination thereof is B, the position B can be identified by movement amount r and movement direction θ from the position A. The determining portion 308 calculates an offset cost $C_n(p)$ based on the offset parameter p in order to obtain an appropriate offset parameter (an offset which enables a user to easily browse the captured image and the defect data while comparing them). Then, the determining portion 308 obtains the offset parameter p which minimizes the offset cost according to Equation 2.

$$p = \underset{o}{\operatorname{argmin}} \left( \sum_n w_n C_n(p) \right) \qquad \text{Equation 2}$$

The offset cost $C_n(p)$ includes offset costs of several different standards described below. Here, $w_n$ is a weight to be applied to each kind of offset cost. Hereinafter, in the present embodiment, three kinds of offsets will be described as examples of the offset cost $C_n(p)$. However, the offset cost calculating method is not limited thereto, and another method may be used.

First, a first offset cost $C_1(p)$ will be described. The first offset cost $C_1(p)$ is defined as an overlap cost with the original position of the object defect data. The reason why the display position of the object defect data is moved is to facilitate the browsing of the captured image of the area where the object defect data are superposed. Therefore, when moving the object defect data from its original position, it is not preferable to move the object defect data to a destination which is a defect area corresponding to the object defect data or to a destination which is a defect area corresponding to another defect data. Therefore, when the object defect data is moved by the offset parameter p, the offset cost $C_1(p)$ is set to a value proportional to the number of overlapping pixels between the display position after the movement and the display position before the movement.

Figure 9A:
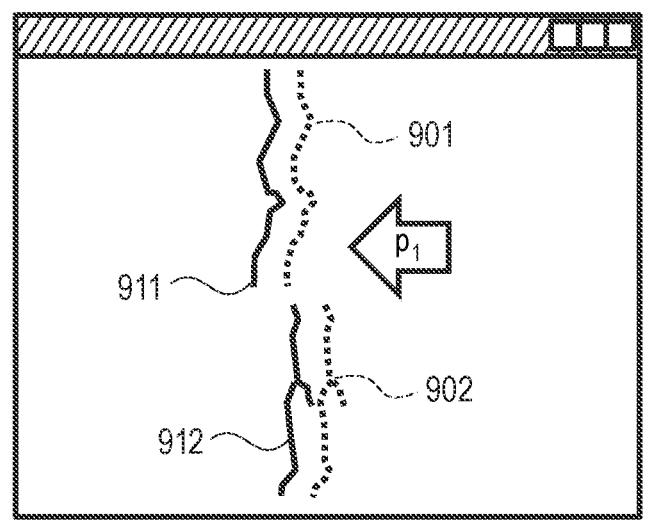
FIG. 9A is a diagram for explaining a relationship between the offset parameter and an offset cost.
Figure 9B:
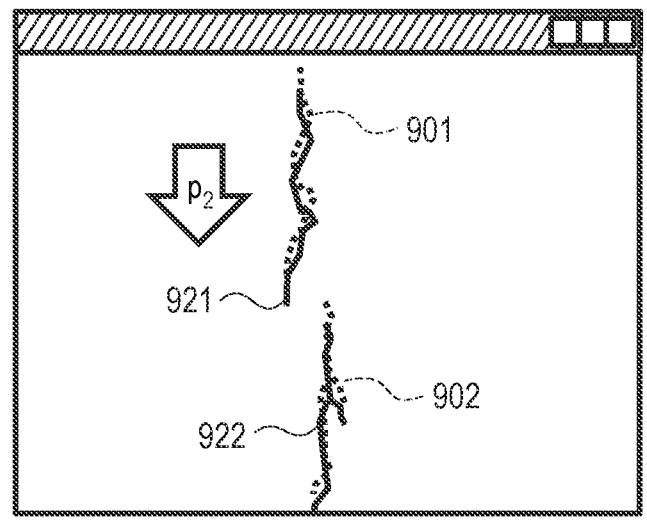
FIG. 9B is a diagram for explaining a relationship between the offset parameter and the offset cost.

Each of FIGS. 9A and 9B is a diagram for explaining a relationship between the offset parameter p and the offset cost $C_1(p)$. First, in each of FIGS. 9A and 9B, positions 901 and 902 indicated by the dotted lines are display positions corresponding to the defect areas. On the other hand, positions 911 and 912 indicated by the solid lines in FIG. 9A are positions after movement according to an offset parameter $p_1$ of the object defect data. Likewise, positions 921 and 922 indicated by the solid lines in FIG. 9B are positions after movement according to an offset parameter $p_2$. In each of FIGS. 9A and 9B, the offset cost $C_1(p)$ is a value proportional to the number of overlapping pixels between the object defect data disposed at the position after the movement and the defect area.

In the example of FIGS. 9A and 9B, the number of overlapping pixels of the positions 921 and 922 of FIG. 9B is larger than the number of overlapping pixels of the positions 911 and 912 of FIG. 9A. Therefore, if it is assumed that the offset cost corresponding to the example of FIG. 9A and the offset cost corresponding to the example of FIG. 9B are $C_1(p_1)$ and $C_1(p_2)$ respectively, then a relationship $C_1(p_1) < C_1(p_2)$ is given. That is, it can be understood that the offset parameter $p_1$ at the position A of FIG. 8 is a desirable parameter, so that the offset parameter $p_1$ for lowering the offset cost is finally selected as represented by Equation (2).

Next, a second offset cost $C_2(p)$ will be described. The second offset cost $C_2(p)$ is a value which is calculated based on the position of an image edge at the position after the movement of the defect data, and becomes larger as the overlap with an edge portion is larger. There is a possibility that an image edge portion of the captured image of the concrete wall surface is a defect such as a crack, a deposit or the like. Therefore, it is a high possibility that the image edge portion like this is an image portion that the user wants to observe, so that it is preferable that the relevant image edge portion is not superposed by defect data.

In order to calculate the offset cost $C_2(p)$, it is first necessary to identify edge pixels of the captured image. For this reason, the information processing apparatus 200 first performs an edge detecting process on the captured image. For the edge detecting method, a known method such as a Sobel filter, Canny or the like may be used. The determining portion 308 sets a value proportional to the number of overlapping pixels of the edge pixels and the defect data moved by the offset parameter p, as an output value of the offset cost $C_2(p)$.

Next, a third offset cost $C_3(p)$ will be described. The third offset cost $C_3(p)$ is calculated according to a distance to the defect area corresponding to the defect data. When the movement amount r of the defect data is small, there is a case where the overlap with the defect area is not eliminated. On the other hand, when the movement amount r is too large, it is difficult to understand a correspondence relationship between the defect area and the defect data, so that it becomes difficult to compare these images. The offset cost $C_3(p)$ is a cost for adjusting the movement amount of the defect data so as to be within a predetermined range.

The offset cost $C_3(p)$ can be calculated, for example, by Equation 3.

$$C_3(p)=(r-\beta)^2 \quad \text{Equation 3}$$

In Equation 3, β is a standard movement amount and is given as a constant. Here, β may be set in any way. For example, the determining portion 308 may determine this amount according to in-browsing resolution (display magnification) of the captured image and defect data. More specifically, the determining portion 308 may set β to a relatively large value when displayed in an enlarged manner, and may set β to a relatively small value when displayed in a reduced manner.

As another example, the determining portion 308 may select the optimum offset parameter p from the predetermined offset parameters p in order to simplify the calculation, as the offset parameter p. For example, as shown in FIG. 10, m offset parameters $p_1$ to $p_m$ are preset in the HDD 204 or the like, and the determining portion 308 obtains the offset parameter p for minimizing Equation 2, from among the m offset parameters.

In the offset parameters $C_1(p)$ and $C_2(p)$, the movement amount r and the movement direction θ of the offset parameter p are obtained. As another example, the determining portion 308 may calculate the offset parameter while setting one of these movement amount and the movement direction as a fixed value. For example, the determining portion 308 may obtain the offset parameter p so as to optimize the movement amount r while always fixing the movement direction θ. Besides, the user may designate the movement direction θ, and the determining portion 308 may calculate only the movement amount r with respect to the movement direction θ designated by the user. Conversely, the user may designate the movement amount, and the determining portion 308 may calculate only the movement direction θ with respect to the movement amount r designated by the user.

Next, a display position changing process of the object defect data in S606 will be described. In S606, the display controlling portion 306 moves the defect data to the display position determined by the offset parameter determined in S605. In the present embodiment, the display controlling portion 306 moves all the defect data being displayed.

As another example, the display controlling portion 306 may move only the object defect data. Further, as another example, the display controlling portion 306 may change the positional relationship between the captured image and the defect data by moving the captured image instead of the defect data in accordance with the offset parameter p.

Figure 11:
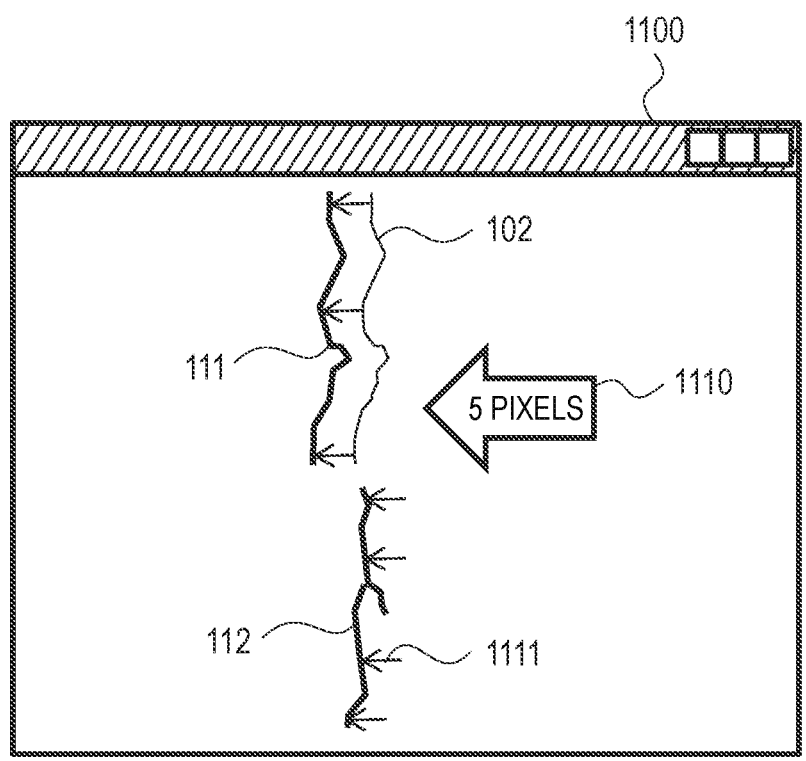
FIG. 11 is a diagram showing an example of a display window.

The created display image is displayed on the displaying unit 205. FIG. 11 is a diagram showing an example in which the display image is displayed on an application window 1100. As compared with FIG. 1C, the defect data 111 and 112 of FIG. 11 are in an offset-displayed state according to the offset parameter p. As a result, the part of the defect area 102, which was difficult to confirm in the simple overlapping display (FIG. 1C), is in a state easy for browsing. Therefore, the user can compare and confirm the defect area 102 of the captured image of the concrete wall surface and the corresponding defect data 111. Also, the user can compare and confirm the area of the captured image corresponding to the defect data 112 corresponding to erroneous detection, and the defect data 112.

Moreover, the display controlling portion 306 may display the defect data together with information such as the offset parameter or the like. In the example of FIG. 11, the movement amount and the movement direction are indicated respectively by the direction and the length of an arrow 1110. The display controlling portion 306 may further display information indicating the correspondence between the defect data and the original position of the offset-displayed defect data. In the example of FIG. 11, the relationship with the original position of the offset-displayed defect data is indicated by a small arrow 1111. Besides, as shown in FIG. 11, the display controlling portion 306 may display the numerical value "5 PIXELS" indicating the movement amount. As another example, the display controlling portion 306 may represent magnitude of the movement amount with luminance or color.

As described above, the information processing apparatus 200 according to the present embodiment selects the object defect data from the defect data, determines the display position after the movement of the object defect data based on the object defect data, and moves and displays the object defect data to the determined display position. Thus, the user can compare and confirm the defect area and the corresponding defect data. In other words, the information processing apparatus 200 can provide a user interface which facilitates confirming operations for a defect (object) in an image and an image showing a defect (object) without requiring user's complicated operations.

As a first modified example of the first embodiment, the information processing apparatus 200 can perform the process related to the embodiment not only to the defect area of the captured image and the corresponding defect data but also to a predetermined area of the captured image and related data related to the predetermined area.

Besides, as a second modified example, the information processing apparatus 200 may switch and display the display position of the defect data by referring to the plurality of offset parameters p. For example, the determining portion 308 calculates the offset cost for each of m offset parameter candidates shown in FIG. 10. Then, the offset parameters of which the cost is equal to or less than a predetermined value are ranked in descending order of cost. Then, the display controlling portion 306 first determines the display position based on the offset parameter having the lowest cost, and controls to display the image in which the defect data is disposed, at the determined display position.

Here, when an offset display change instruction is accepted from the user, the display controlling portion 306 determines the display position based on the second offset parameter, and controls to display the image in which the defect data is disposed, at this determined display position. As just described, the display controlling portion 306 may change the display position of the defect data by changing the offset parameter in rank order each time the instruction is accepted from the user. Thus, the user can display the defect data at a desired position.

Figure 12:
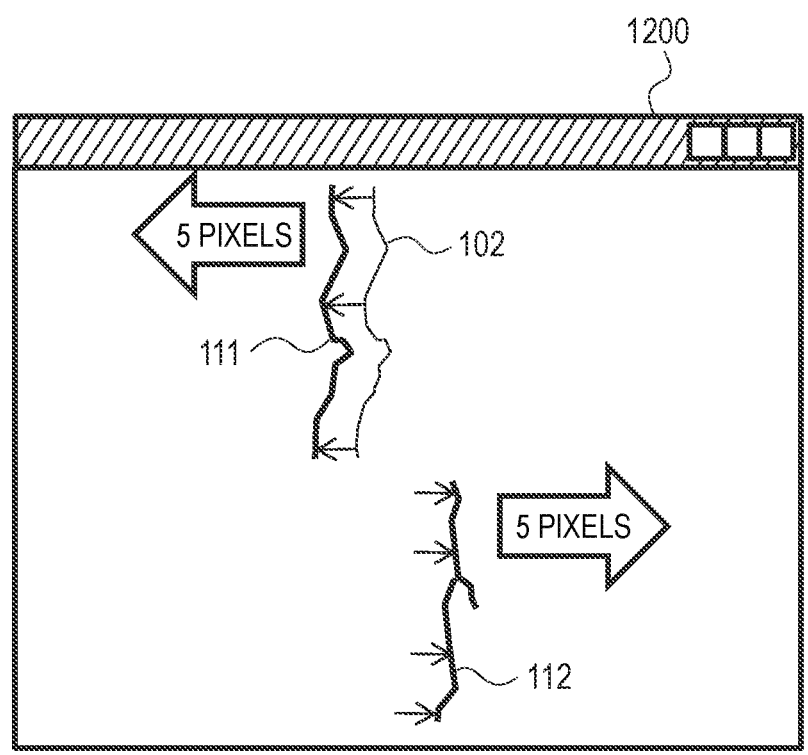
FIG. 12 is a diagram showing an example of the display window.

Besides, as a third modified example, the information processing apparatus 200 may individually calculate the offset parameter for each object defect data when the plurality of object defect data are selected. Then, the information processing apparatus 200 may determine the display position after the movement of the defect data by using the offset parameter corresponding to each defect data. The defect data 111 and 112 in a window 1200 of FIG. 12 are moved based on appropriate offset parameters respectively. This is the case where the offset parameter in the opposite direction to the defect data 111 is calculated for the defect data 112, for example, due to an influence of the image edge of the captured image of the concrete wall surface, or the like.

Besides, as a fourth modified example, the determining portion 308 may correct the automatically calculated offset parameter, in response to a user operation. The display controlling portion 306 displays the movement amount r and the movement direction θ of the automatically calculated offset parameter, in the field on the GUI. A user, who desires to display the defect data with an offset parameter different from the automatically calculated offset parameter, performs input for changing the values of the movement amount r and the movement direction θ displayed in the field. Thus, the user can perform the browsing by correcting the automatically calculated offset parameter. Also, the process related to the correction of the offset parameter by the user is not limited to the numerical value input to the GUI field. As another example, the display controlling portion 306 may display the parameters in a GUI bar so that the user can correct the parameters by moving the bar.

Second Embodiment

Next, the information processing apparatus 200 according to the second embodiment will be described. The information processing apparatus 200 according to the second embodiment obtains a main line direction of the object defect data, and calculates the offset parameter based on the obtained main line direction. Hereinafter, such an operation will be described by taking a crack as an example. Incidentally, the information processing apparatus 200 according to the second embodiment determines the offset parameter p by fixing the movement amount r and obtaining the movement direction θ.

Figure 13:
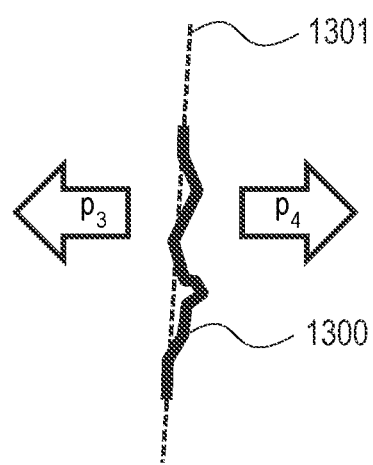
FIG. 13 is a diagram for explaining a method of calculating the offset parameter.

FIG. 13 is a diagram for explaining a method of calculating the offset parameter p in a case where a crack object defect data 1300 is selected. The determining portion 308 first calculates a main line direction of the object defect data 1300. In FIG. 13, the main line direction of the object defect data 1300 is indicated by a dotted line 1301. Although the main line direction 1301 may be calculated in any way, for example, it is possible to simply obtain this direction by connecting the start point and the end point of the object defect data 1300.

Then, the determining portion 308 obtains a direction orthogonal to the main line direction 1301 as the movement direction θ. For the crack 1300, two movement directions are obtained, and corresponding to these directions, offset parameters $p_3$ and $p_4$ are calculated as shown in FIG. 13.

Thereafter, the display controlling portion 306 controls to create an image in which the defect data is moved by one of the offset parameters, and display the created image on the displaying unit 205. Then, when the user inputs a change of the offset parameter, the display controlling portion 306 controls to create an image in which the defect data is moved by the other offset parameter, and display the created image.

Incidentally, other constitutions, configurations and processes of the information processing apparatus 200 according to the second embodiment are similar to those of the information processing apparatus 200 according to the first embodiment. As just described, the information processing apparatus 200 according to the present embodiment can determine the offset parameter according to the main line direction of a defect. Therefore, it is possible to display the defect data at an appropriate position.

As a modified example of the second embodiment, a plurality of defect data may be selected as the object defect data. In this case, the determining portion 308 calculates the main line direction of each of the plurality of object defect data (cracks). The determining portion 308 then determines the offset parameter p with the direction orthogonal to a statistical main line direction obtained from the plurality of main line directions as the movement direction θ. Here, the statistical main line direction is, for example, a direction obtained by an average value or a median value in the plurality of main line directions.

Third Embodiment

Next, the information processing apparatus 200 according to the third embodiment will be described. The information processing apparatus 200 according to the third embodiment automatically selects the object defect data based on an attribute of the defect data. The attributes of the defect data to be referred to are as follows. First, it is assumed that the defect is a crack and each crack has crack thickness attribute information as shown in FIG. 4. In this case, the selecting portion 307 refers to a thickness attribute, and selects relatively a thin crack as the object defect data because of the following reason. That is, an input operator's error and an automatic detection error are likely to occur with respect to the thin crack because it is difficult to decide whether or not the thin crack is a crack. Therefore, the thin crack is the defect which should be confirmed in detail.

Also, it is often difficult to decide whether or not a crack overlapping a deposit or the like is a crack. Therefore, the determining portion 308 refers to attribute information indicating whether the crack overlaps the deposit, and selects the crack having an overlap as the object defect data. In this case, it is assumed that the attribute information indicating whether the crack overlaps the deposit is stored as the defect data in the defect data storing portion 302.

Besides, the detecting portion 304 may automatically detect the defect data and further obtain a score indicating reliability of a detection result. Further, the selecting portion 307 may select, as the object defect data, the defect data corresponding to a defect area of a relatively low score such as a score being less than a threshold. When the reliability score is low, it is preferable for the user to confirm the automatic detection result. By selecting the corresponding defect data as the object defect data, it is possible to perform a detailed confirmation preferentially.

Incidentally, other constitutions, configurations and processes of the information processing apparatus 200 according to the third embodiment are similar to those of the information processing apparatuses 200 according to other embodiments. In the information processing apparatus 200 according to the third embodiment, it is possible to select an appropriate defect area without requiring a user operation.

As a modified example of the third embodiment, the selecting portion 307 may determine the attribute information to be referred to when selecting object defect data, in accordance with a user's browsing state. For example, the selecting portion 307 selects the cracked defect data when the captured image is being browsed with high resolution (enlarged size), whereas selects the defect data having the area of the deposit or the like when the captured image is being browsed with low resolution (reduced size). When the captured image is being browsed with high resolution, it is highly likely that the user is confirming the fine defect such as a crack. On the contrary, when the captured image is being browsed with low resolution, since a wide area is being browsed, it is highly likely that the user is confirming the spread defect such as a deposit or the like. Under such circumstances, the object data to be selected can be changed according to the user's browsing state.

Fourth Embodiment

Next, the information processing apparatus 200 according to the fourth embodiment will be described. In the fourth embodiment, transparency $\alpha$ will be described as an example of a display parameter other than the offset parameter. The display controlling portion 306 calculates the transparency $\alpha$ as the display parameter, and changes the transparency of the defect data around the object defect data. Thus, it becomes possible for the user to more easily browse the object defect data. Here, the display parameter is a parameter for making a display form of the object defect data different from those of other defect data.

Figure 14A:
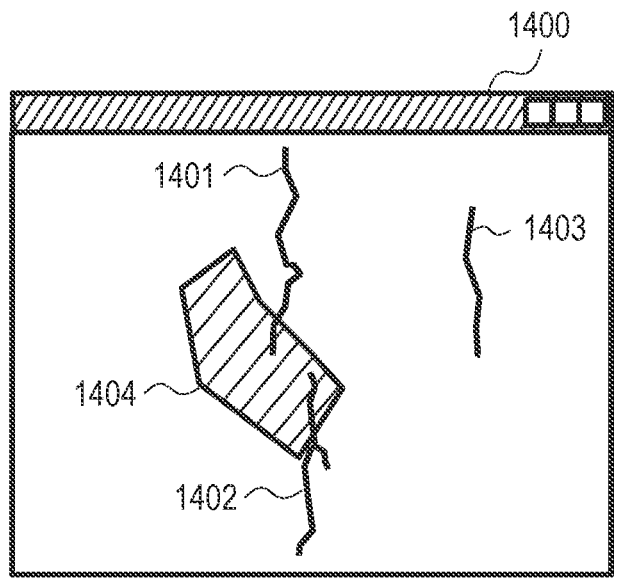
FIG. 14A is a diagram showing an example of the display window.
Figure 14B:
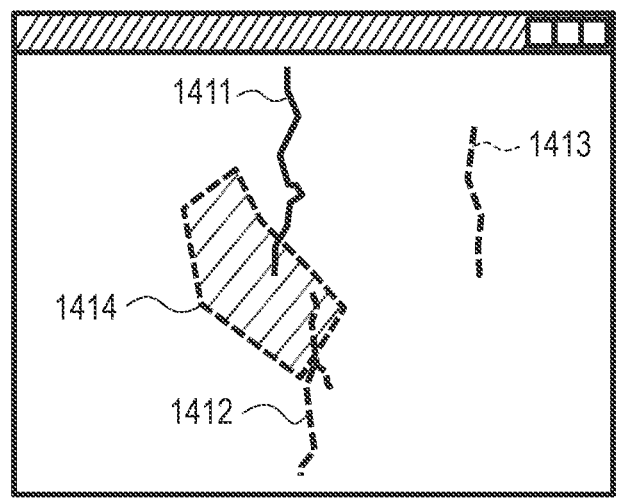
FIG. 14B is a diagram showing an example of the display window.

FIGS. 14A and 14B are diagrams for explaining the present embodiment. FIG. 14A is the diagram showing an example in which a plurality of defect data are displayed close to others, that is, cracked defect data 1401, 1402 and 1403 and deposit defect data 1404 are displayed close to others. Here, it is assumed that the defect data 1401 is selected as the object defect data by a user's selection or the like. In this regard, the display controlling portion 306 sets the display parameter of the transparency $\alpha$ for the defect data other than the object defect data, that is, other defect data. It is assumed that the transparency $\alpha$ is set by the user through numerical input, or input by the user through a parameter bar on the GUI. The transparency $\alpha$ is a value indicating a degree of transparent display, and is a parameter having a value of 0% to 100%. The display controlling portion 306 sets the transparency $\alpha$ of other defect data to a preset value (for example, 50%). Thus, it is possible to create a display image through which other defect data have been transmitted.

FIG. 14B is the diagram showing a state in which defect data other than object defect data 1411 are displayed in a transparent state by such a process as described above. Other defect data 1412, 1413 and 1414 indicated by the dotted lines indicate that these other defect data are displayed in the transparent state. By performing display in this way, the user can confirm only the object defect data 1411 in detail. In particular, the object defect data 1411 overlaps the another defect data (deposit) 1414. Therefore, by making the display of the another defect data 1414 transmittable, it is possible to confirm the overlap portion in detail.

Besides, the display controlling portion 306 may set the transparency $\alpha$ according to a distance between the object defect data and another defect data. For example, the display controlling portion 306 sets a higher degree of transparency as the distance to the object defect data is closer. Thus, the display controlling portion 306 can create a display image in which other defect data in the vicinity of the object defect data are made transparent (non-display) and such other defect data are displayed as they become away peripherally. As a result, the user can easily browse the object defect data and can confirm the surrounding defect data. Incidentally, other constitutions, configurations and processes of the information processing apparatus 200 according to the fourth embodiment are similar to those of the information processing apparatuses 200 according to other embodiments. As just described, the information processing apparatus 200 according to the fourth embodiment can improve visibility of the object defect data by increasing the transparency of other defect data.

As a first modified example of the fourth embodiment, the display controlling portion 306 may change the transparency of the object defect data instead of changing the transparency of other defect data. As just described, the transparency of the object defect data and the transparency of other defect data may be made different. As another example, the display controlling portion 306 may select whether to change the transparency object to the object defect data or another defect data, according to a user instruction.

As described above, in the fourth embodiment, the example in which the transparency $\alpha$ is used as the display parameter other than the offset parameter has been described. As a second modified example, the display parameter other than the offset parameter is not limited to the transparency $\alpha$, and another parameter may be used. For example, the information processing apparatus 200 may change blurring intensity $\sigma$ as the display parameter. The blurring intensity $\sigma$ is a parameter indicating the width of a Gaussian filter, and as a larger value is set, a blurred image can be created. The display controlling portion 306 sets a larger value to the blurring intensity $\sigma$ of another defect data, as the distance from the object defect data is closer. Thus, it is possible to create a display image in which other defect data are blurred.

Fifth Embodiment

Next, the information processing apparatus 200 according to the fifth embodiment will be described. In the information processing apparatus 200 according to the fifth embodiment, the determining portion 308 first calculates the offset parameter p. At this time, there is a case where the movement amount r of the offset parameter p becomes a small value. When the movement amount r is the small value, the defect data hardly moves from its original position. Therefore, it is difficult to browse the captured image of the area superposed on the defect data. Under such circumstances, in the present embodiment, when the movement amount r is equal to or less than a threshold, the display controlling portion 306 changes the transparency $\alpha$ of the object defect data.

For example, the display controlling portion 306 sets a higher transparency $\alpha$ with respect to the object defect data as the movement amount r is smaller. The reason why the higher transparency $\alpha$ is set as the movement amount r is smaller is to facilitate the browsing of the captured image of the area on which the object defect data is superposed. Thus, the object defect data slightly moves according to the offset parameter p, and is displayed in a transparent state according to the transparency α. Thus, even when the movement amount from the original position is small, it is possible to facilitate the browsing of the captured image of the area on which the object defect data is superposed.

Incidentally, other constitutions, configurations and processes of the information processing apparatus 200 according to the fifth embodiment are similar to those of the information processing apparatuses 200 according to other embodiments. As just described, the information processing apparatus 200 according to the fifth embodiment changes the transparency of the object defect data at the same time as changing the offset parameter, so that it is possible to facilitate the browsing of the captured image of the area on which the object defect data is superposed.

As a modified example of the fifth embodiment, the display parameter is not limited to the transparency α. Another example is the blurring intensity σ. As another display parameter, the display controlling portion 306 may use a period display flag which periodically turns on and off an object display image. In this case, when an offset parameter of which the movement amount r is small is calculated, the display controlling portion 306 sets the period display of the objective defect data to be on, and controls to blinking-display the object defect data. Thus, even when the movement amount r is small, it is possible to facilitate the browsing of the captured image of the area on which the object defect data is superposed.

Sixth Embodiment

Figure 15A:
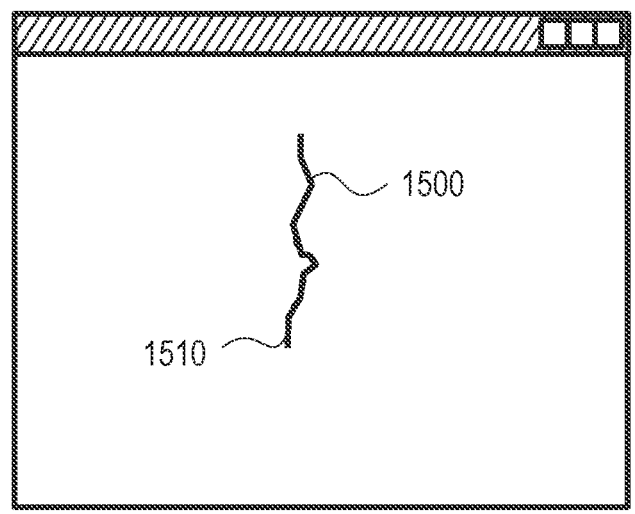
FIG. 15A is a diagram showing an example of the display window.
Figure 15B:
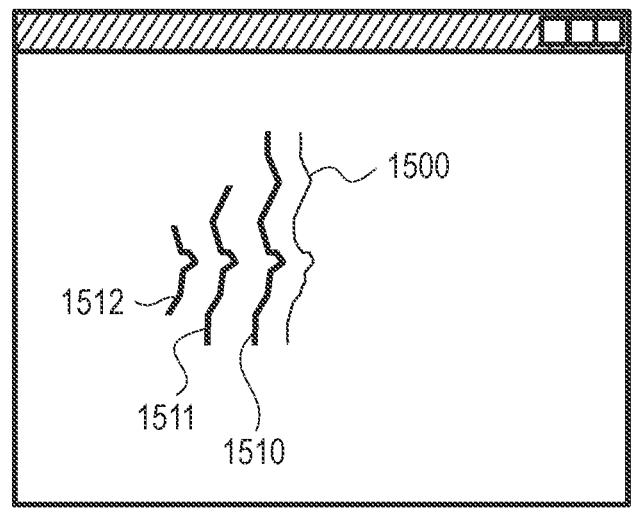
FIG. 15B is a diagram showing an example of the display window.

Next, the information processing apparatus 200 according to the sixth embodiment will be described. The information processing apparatus 200 according to the sixth embodiment arranges and displays a plurality of defect data of different sources in the vicinity of the defect area. FIGS. 15A and 15B are diagrams showing an example of arranging and offset-displaying the defect data respectively created at different times. For example, it is assumed that the defect data of the concrete wall surface of an object structure corresponding to biennial detection results of 2012, 2014 and 2016 are stored. In order to confirm aging defect of the structure, the defect data at different times are recorded as described above. Like this, it is assumed that such defect data of the different sources are stored in the defect data storing portion 302.

In FIG. 15A, first, defect data 1510 corresponding to the defect data recorded in 2016 is superposed and displayed on a defect area 1500 of the concrete wall surface image. FIG. 15B shows a display image to be displayed when the user issues a display change command in a state where the defect data 1510 is selected as the object defect data in FIG. 15A. In FIG. 15B, three defect data 1510, 1511 and 1512 are displayed with respect to the defect area 1500. The defect data 1511 is the defect data corresponding to the record of 2014, and the defect data 1512 is the defect data corresponding to the record of 2012. The defect data 1510, 1511 and 1512 are offset displayed in the order of the recording year.

The information processing apparatus 200 according to the sixth embodiment calculates the offset parameter p of the defect data 1510 corresponding to the latest record by the process described in the first embodiment, and displays the defect data 1510. Further, the information processing apparatus 200 displays the past defect data 1511 and 1512 by further offsetting them in the direction of the movement direction θ of the offset parameter p of the defect data 1510. In a case where there are the plurality of past defect data, it is preferable to display the plurality of defect data in chronological order, as shown in FIG. 15B.

Besides, the information processing apparatus 200 may display the plurality of defect data along the time series so as to have the same interval, or may display the plurality of defect data so as to have intervals according to the respective capturing times of these data. Thus, the user can easily confirm a secular change of the defect area. Incidentally, other constitutions, configurations and processes of the information processing apparatus 200 according to the sixth embodiment are similar to those of the information processing apparatuses 200 according to other embodiments.

Figure 16:
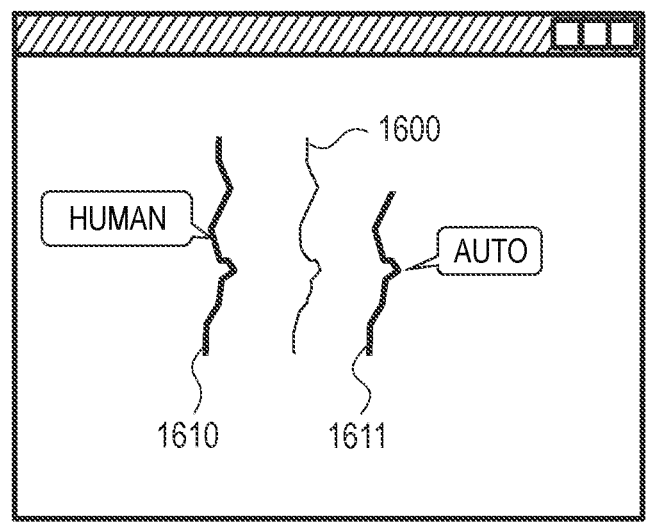
FIG. 16 is a diagram showing an example of the display window.

A modified example of the sixth embodiment will be described. In a case where an input result by an input operator and an automatic detection result are respectively recorded in the same defect area, the information processing apparatus 200 may display the two defect data corresponding to these two detection results. FIG. 16 is a diagram showing an example in which defect data 1610 corresponding to the defect data input by the input operator and defect data 1611 corresponding to the automatic detection result are simultaneously offset-displayed in a defect area 1600 of the captured image.

In FIG. 16, the defect data 1610 and 1611 are displayed on the opposite sides of the defect area 1600. To display the two defect data in this manner, for example, the offset parameters $p_3$ and $p_4$ described in the second embodiment may be applied. As another example, the information processing apparatus 200 may arrange and display the defect data 1610 corresponding to the defect data input by the input operator and the defect data 1611 corresponding to the automatic detection result in the same direction.

Incidentally, the defect data to be simultaneously arranged and displayed are not limited to those in the embodiment. As another example, the information processing apparatus 200 may simultaneously display the defect data input by a plurality of different input operators. Thus, it is possible to compare and confirm a plurality of defect data having different creation steps.

As a second modified example, the information processing apparatus 200 may display the defect data respectively created at different times or the defect data of the different sources, in a displaying method other than the offset display. For example, the information processing apparatus 200 may assign and display different colors respectively to the defect data created at different times or the defect data of the different sources. More specifically, for example, the information processing apparatus 200 performs color coding to the defect data respectively created at different times, sets the new defect data as a lower layer, sets the old defect data as an upper layer, and displays them. Thus, it becomes possible to confirm a status of progress of defect.

As just described, according to each of the above embodiments, it is possible to provide the user interface which facilitates the confirming operation for the area in the image and the associated data corresponding to the area without requiring user's complicated operations.

Although the present invention has been described in detail based on the preferred embodiments thereof, the present invention is not limited to these specific embodiments. Namely, various embodiments within the scope not deviating from the subject matter of the present invention are also included in the present invention. For example, parts of the above embodiments may be appropriately combined. Namely, the individual offset parameter according to the main line direction may be set for each of the plurality of object areas, by combining the second embodiment with the second modified example of the first embodiment.

Further, in each of the above embodiments, the case where the image indicating the defect is superposed and displayed on the captured image obtained by capturing the infrastructure structure has been described. However, the present invention is not limited to these embodiments. For example, the present invention can also be applied to a case where an image indicating the position of a blood vessel is superposed and displayed in a medical image including the blood vessel. That is, the present invention can be widely applied to an embodiment in which an image indicating the positions of a plurality of objects are superposed and displayed on an image including the plurality of objects (defect in a structure, a blood vessel, and the like). Therefore, "defect" in each of the above embodiments is an example of "object" in the present invention.

Other Examples

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

According to the present invention, it is possible to provide a user interface which facilitates a confirming operation of an area in an image and associated data corresponding to the area without requiring use's complicated operations.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:
1. An information processing apparatus comprising
one or more processors; and
one or more memories,
the one or more processors functioning as following units by executing instructions stored in the one or more memories:
an obtaining unit configured to obtain a first image including one or more objects which are defects on a structure, and information related to positions in the first image of the one or more objects or ranges in the first image of the one or more objects;
a display control unit configured to cause a displaying unit to display defect data being drawing of the one or more objects based on the information, so as to be superposed on the first image at a first position according to the position or the range indicated by the information; and
a determining unit configured to determine, in the first image, a second position that is a position at which an overlap between the one or more objects in the first image and the defect data is small, in an occasion that a case where the defect data is displayed at the first position is compared with a case where the defect data is displayed at the second position,
wherein the display control unit is configured to perform control to switch the display of the defect data at the first position to the display of the defect data at the second position.

2. The information processing apparatus according to claim 1, wherein the determining unit is configured to determine a position shifted from the positions of the one or more objects in the first image in a direction based on shapes of the one or more objects, as a position at which data is superposed on the first image.

3. The information processing apparatus according to claim 1, wherein the one or more processors further function as a calculating unit configured to calculate an evaluation value related to a relationship between the one or more objects included in the first image and the defect data, wherein
the determining unit is configured to determine the second position when superposing and displaying the first image and the defect data, based on the evaluation value calculated by the calculating unit.

4. The information processing apparatus according to claim 3, wherein the evaluation value is calculated based on at least one of a value related to an overlap between the one or more objects included in the first image and the defect data, a value related to an overlap between an edge of the first image and the defect data, and a value related to a distance between the one or more objects included in the first image and the defect data.

5. The information processing apparatus according to claim 1, wherein the one or more processors further function as an identifying unit configured to identify a predetermined area in the first image, wherein
the one or more objects are included in the predetermined area.

6. The information processing apparatus according to claim 5, wherein the identifying unit is configured to identify the predetermined area based on the object designated in the first image by a user.

7. The information processing apparatus according to claim 5, wherein the identifying unit is configured to identify the predetermined area based on an attribute of the one or more objects included in the first image.

8. The information processing apparatus according to claim 1, wherein the one or more processors are configured to determine a first display state that the one or more objects in the first image and the defect data are shifted and superposed at the first position or a second display state that the one or more objects in the first image and the defect data are superposed without shifted at the second position, as a display form when displaying the first image and the defect data.

9. The information processing apparatus according to claim 8, wherein the display control unit is configured to switch the first display mode and the second display mode based on a user instruction.

10. The information processing apparatus according to claim 1, wherein the determining unit is configured to further determine at least either transparency or blurring intensity of the defect data.

11. The information processing apparatus according to claim 1, wherein the one or more objects are cracks of the structure.

12. An information processing method comprising:
obtaining a first image including one or more objects which are defects on a structure, and information related to positions in the first image of the one or more objects or ranges in the first image of the one or more objects;
causing a displaying unit to display defect data being drawing of the one or more objects based on the information, so as to be superposed on the first image at a first position according to the position or the range indicated by the information; and
determining, in the first image, a second position that is a position at which an overlap between the one or more objects in the first image and the defect data is small, in an occasion that a case where the defect data is displayed at the first position is compared with a case where the defect data is displayed at the second position,
wherein it is controlled to switch the display of the defect data at the first position to the display of the defect data at the second position.

13. A non-transitory computer-readable storage medium which stores a program for causing a computer to function as:
an obtaining unit configured to obtain a first image including one or more objects which are defects on a structure, and information related to positions in the first image of the one or more objects or ranges in the first image of the one or more objects;
a display control unit configured to cause a displaying unit to display defect data being drawing of the one or more objects based on the information, so as to be superposed on the first image at a first position according to the position or the range indicated by the information; and
a determining unit configured to determine, in the first image, a second position that is a position at which an overlap between the one or more objects in the first image and the defect data is small, in an occasion that a case where the defect data is displayed at the first position is compared with a case where the defect data is displayed at the second position,
wherein the display control unit is configured to perform control to switch the display of the defect data at the first position to the display of the defect data at the second position.

14. The information processing apparatus according to claim 2, wherein the direction is determined based on a main line direction of at least one of the one or more objects.

15. The information processing apparatus according to claim 1, wherein the determining unit is configured to determine a position shifted from the positions of the one or more objects in the first image in a direction determined based on a main line direction of the one or more objects, as a position at which data is superposed on the first image.

16. The information processing apparatus according to claim 1, wherein the display control unit is configured to cause the displaying unit to display a first defect data indicating a first defect captured at a first time and a second defect data corresponding to the first defect captured at a second time later than the first time.

17. The information processing apparatus according to claim 1, wherein the determining unit is configured to determine the second position, such that the number of overlapping pixels becomes small as compared with the number of overlapping pixels between the defect data and the one or more objects in the first image in the case where the defect data is superposed at the first position in the first image.

18. The information processing apparatus according to claim 3, wherein
the one or more objects are cracks of the structure, and
in case of displaying the first image and the defect data, the defect data obtained by drawing the crack indicated by the information with a color corresponding to a thickness is displayed.

19. The information processing apparatus according to claim 1, wherein the determining unit is configured to determine the second position, such that the one or more object in the first image and the defect data do not overlap.

* * * * *